United States Patent
Danzer et al.

(10) Patent No.: US 11,326,115 B2
(45) Date of Patent: *May 10, 2022

(54) BIODIESEL COLD FILTRATION PROCESS

(71) Applicants: REG Biofuels, LLC, Ames, IA (US); Crown Iron Works Company, Roseville, MN (US)

(72) Inventors: Myron Francis Danzer, Glidden, IA (US); Timothy L Ely, Jefferson, IA (US); Scott Alan Kingery, Jefferson, IA (US); John Mostek, Carroll, IA (US); Matthew Leonard Schultes, Carroll, IA (US); Wayne William McCalley, Andover, MN (US); William Michael McDonald, Maplewood, MN (US)

(73) Assignee: Renewable Energy Group, Inc., Ames, IA (US)

( * ) Notice: Subject to any disclaimer, the term of this patent is extended or adjusted under 35 U.S.C. 154(b) by 714 days.

This patent is subject to a terminal disclaimer.

(21) Appl. No.: 14/809,472

(22) Filed: Jul. 27, 2015

(65) Prior Publication Data

US 2015/0329791 A1  Nov. 19, 2015

Related U.S. Application Data

(63) Continuation of application No. 11/670,153, filed on Feb. 1, 2007, now Pat. No. 9,109,170.

(Continued)

(51) Int. Cl.
*C10L 1/02* (2006.01)
*C07C 67/56* (2006.01)
(Continued)

(52) U.S. Cl.
CPC .............. *C10L 1/026* (2013.01); *B01D 15/08* (2013.01); *B01D 17/00* (2013.01); *B01D 21/0012* (2013.01); *B01D 29/56* (2013.01); *C07C 67/56* (2013.01); *C10G 31/09* (2013.01); *C11C 1/08* (2013.01); *C11C 3/003* (2013.01); *C10G 2300/1011* (2013.01); *C10G 2400/04* (2013.01); *C10L 2200/0476* (2013.01);
(Continued)

(58) Field of Classification Search
CPC .............. C10L 1/026; C10L 2200/0476; C10L 2270/026; C10L 2290/542; C10L 2290/547; B01D 15/08; B01D 21/0012; B01D 29/56; B01D 17/00; C07C 67/56; C11C 1/08; C11C 3/003; C10G 31/09; C10G 2300/1011; C10G 2400/04; Y02P 30/20; Y02E 50/10
See application file for complete search history.

(56) References Cited

U.S. PATENT DOCUMENTS

| 2005/0188607 A1* | 9/2005 | Lastella | C10L 1/026 44/605 |
| 2006/0063242 A1* | 3/2006 | Chou | C11C 3/003 435/135 |

FOREIGN PATENT DOCUMENTS

WO  WO-2005037969 A2 *  4/2005  .............. B01J 20/10

* cited by examiner

*Primary Examiner* — Latosha Hines
(74) *Attorney, Agent, or Firm* — Nyemaster Goode, PC

(57) ABSTRACT

An improved biodiesel production process includes the steps of processing a feedstock to produce biodiesel, cooling the biodiesel so as to form sediment, and filtering the biodiesel to remove the sediment. The resulting biodiesel from the cold filtration process avoids problems of sediment formation during storage and transportation.

22 Claims, 2 Drawing Sheets

BIODIESEL PRODUCTION PROCESSES

Related U.S. Application Data

(60) Provisional application No. 60/764,440, filed on Feb. 2, 2006.

(51) Int. Cl.
*C11C 1/08* (2006.01)
*C11C 3/00* (2006.01)
*B01D 15/08* (2006.01)
*B01D 21/00* (2006.01)
*B01D 29/56* (2006.01)
*B01D 17/00* (2006.01)
*C10G 31/09* (2006.01)

(52) U.S. Cl.
CPC ... *C10L 2270/026* (2013.01); *C10L 2290/542* (2013.01); *C10L 2290/547* (2013.01); *Y02E 50/10* (2013.01); *Y02P 30/20* (2015.11)

BIODIESEL COLD FILTRATION PROCESS

CROSS-REFERENCE TO RELATED APPLICATIONS

This application is a continuation of U.S. patent application Ser. No. 11/670,153 filed on Feb. 1, 2007 which claims priority under 35 U.S.C. § 119 to provisional application Ser. No. 60/764,440 filed Feb. 2, 2006, which applications are hereby incorporated by reference in their entirety.

FIELD OF THE INVENTION

The invention relates to an improved process for producing biodiesel fuel. More particularly, the quality of the biodiesel fuel is improved by using a cold filtration process to remove non-methyl ester impurities and other contaminants, such as sterol glycosides and other unsaponifiables.

BACKGROUND OF THE INVENTION

There is significant interest in alternative fuels which are non-petroleum based for many reasons, including environmental, economic, political, and other reasons. Biodiesel fuel is one alternative based upon renewable resources. Biodiesel is a mono-alkyl ester of long chain fatty acids, such as methyl ester derived from fats and oils, and provides lower emissions as compared to petroleum-based diesel fuel. The cetane number, energy content, viscosity, and phase changes of biodiesel are similar to petroleum diesel.

Biodiesel is derived from a transesterification chemical process wherein the triglyceride feedstock, such as fat or vegetable oil, is processed for conversion into methyl esters (biodiesel) and glycerin.

The American Society for Testing Materials (ASTM) has developed standards for biodiesel fuels, with the most common being D-6751. ASTM standard D-6751 sets commercial quality specifications required for biodiesel fuel. The D-6751 standard requires water and sediment be less than 0.050%, by volume, as measured by ASTM standard D-2709. However, biodiesel which meets the D-6751 ASTM standard can still contain contaminants which tend to crystallize and/or form and drop out of solution as sediment. When such biodiesels are used at lower temperatures, the precipitates create problems by decreasing the fuel flow and by clogging fuel lines, filters, and other components of the engines burning the fuel.

Therefore, a primary objective of the present invention is the provision of a process for producing biodiesel which eliminates or minimizes the precipitation problems of this alternative fuel.

Another objective of the present invention is the provision of an improved biodiesel production process which utilizes cold filtration for removing impurities and contaminants from the biodiesel.

Still another objective of the present invention is the provision of a method for improving the quality of biodiesel by removing particulates therefrom prior to storage or transportation.

Yet another objective of the present invention is the provision of a process for cooling and filtering biodiesel for the removal of formed sediments.

Another objective of the present invention is the provision of an improved biodiesel production process which removes non-methyl esters and sterol glycosides from the biodiesel.

Still another objective of the present invention is a method of producing biodiesel by cooling the biodiesel with one or more heat exchangers which can be quickly and easily cleaned.

These and other objectives will become apparent from the following description of the invention.

BRIEF SUMMARY OF THE INVENTION

The improved biodiesel production process of the present invention uses cold filtration to remove impurities and contaminants from the biodiesel. After the triglyceride feedstock is processed for separation into methyl esters and glycerin, the methyl ester biodiesel is cooled to a temperature of less than about 38° C. (100° F.) so that the impurities and contaminants precipitate out as particulates in the biodiesel liquid. Diatomaceous earth or other filtering material is then added to the cooled biodiesel to form a slurry, which is then filtered through a pressure leaf or other type of filter to remove the particulates. The filtered biodiesel is then run through a polish filter to remove any remaining sediments and diatomaceous earth, so as to produce the final biodiesel product.

DETAILED DESCRIPTION OF THE PREFERRED EMBODIMENT

Figure 1:
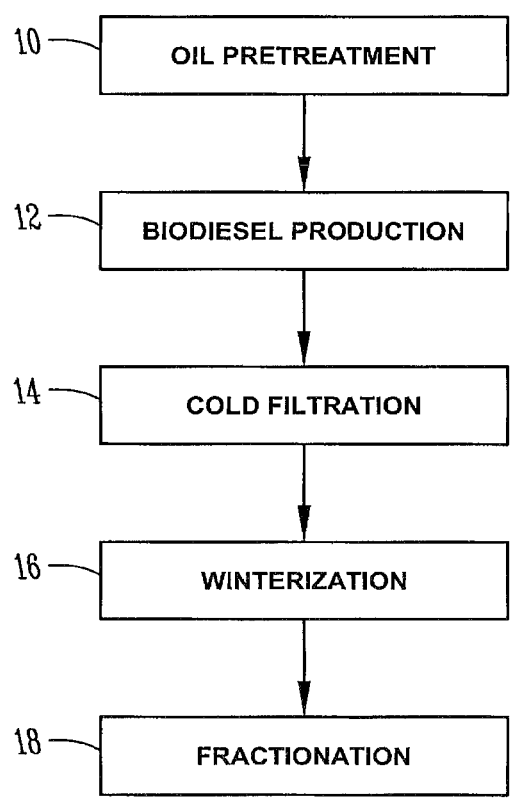
FIG. 1 is a schematic view showing a preferred embodiment of the biodiesel production process according to the present invention.

FIG. 1 shows a preferred process for producing improved quality biodiesel, including the novel cold filtration step of the present invention. The process includes five general steps, including the pretreatment step 10, the biodiesel production step 12, the cold filtration step 14, the optional winterization step 16, and the optional fractionation step 18. The pretreatment step 10, biodiesel production step 12, and winterization and fractionation steps 16, 18 are known in the industry. The improved quality biodiesel is a result of the cold filtration step 14.

The purpose of the pretreatment step 10 is to remove contaminants and impurities, such as phospholipid gums and free fatty acids, from the triglyceride feedstock, so as to clean up the feedstock in preparation for the biodiesel production step 12. Conventional technology is used in this pretreatment step 10, such as degumming, caustic refining, and silica adsorbent filtration.

The biodiesel production step 12 converts the triglycerides into methyl esters (also known as biodiesel) and glycerin. The conventional technology for this production step 12 utilizes transesterification reaction with methanol in the presence of a sodium methoxide catalyst so as to separate the methyl esters from the glycerin.

The winterization step 16 is optional, depending upon the climate in which the biodiesel is to be used. The purpose of winterization is to improve the cold flow and winter performance of the fuel. The winterization step 16 removes saturated methyl esters, such as C16:0 methyl palmitate and C18:0 methyl stearate, though such removal is indiscriminate. The winterization technology is conventional, and utilizes the crystallization of saturates by controlling the time, temperature and agitation of the biodiesel. The crystals are then removed by decantation and filtration.

The fractionation step 18 is also optional, depending upon the temperatures in which the biodiesel is to be used. Fractionation improves the cold flow and winter performance of the fuel, by selectively separating methyl esters into individual components or fractions. Conventional fractionation technology is utilized, including urea fractionation, solvent fractionation, or thermal distillation.

The biodiesel production process of the present invention improves the quality of the biodiesel by adding the novel cold filtration step 14. The purpose of the cold filtration step 14 is to clean up the biodiesel fuel by removing trace contaminants, including sterol glycosides and other unsaponifiables which are naturally present, as well as non-methyl ester impurities. The cold filtration step 14 generally involves cooling the biodiesel to at least about 70° F. (about 21° C.), adding diatomaceous earth or other adsorbent to the biodiesel to form a slurry, and filtering the slurry through a pressure leaf or other type of filter to remove solids formed during the cooling of the biodiesel.

Figure 2:
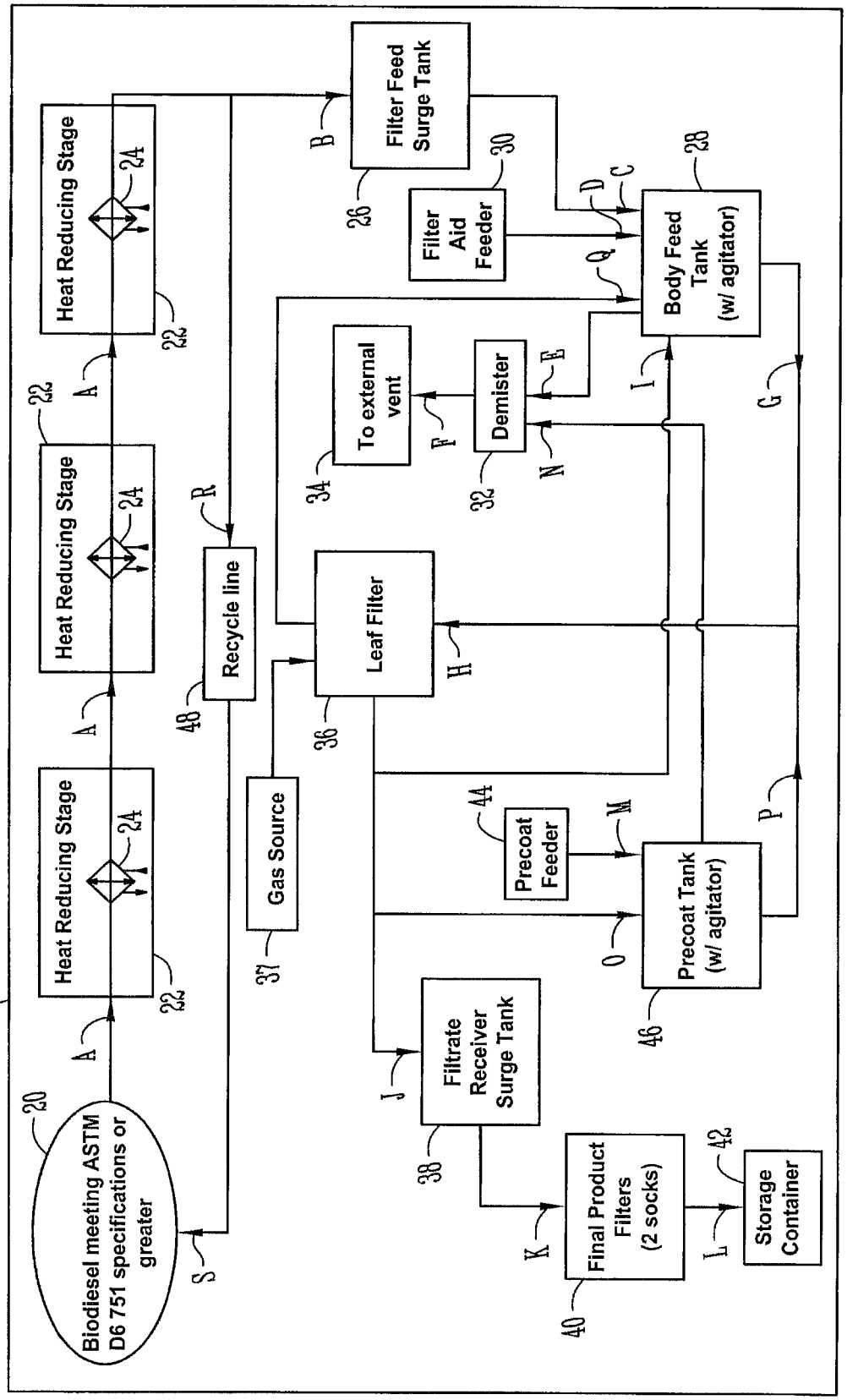
FIG. 2 is a schematic view showing a preferred embodiment of the cold filtration step in the biodiesel production process of the present invention.

The cold filtration step 14 is shown in greater detail in FIG. 2. The biodiesel 20 resulting from the production step 12 is first cooled through one or more stages 22, as indicated by arrow A. Any conventional cooling systems can be utilized, such as heat exchangers 24. Typically, the biodiesel produced by the production step 12 is approximately 290° F. (143° C.), or more. At the end of the cooling stage or stages 22, the temperature is preferably between about 40-100° F. (4-38° C.), with about 65-80° F. (18-27° C.) being preferred, with a most preferred temperature of approximately 70° F. (22° C.). For example, in one embodiment, an economizer is used in a first cooling stage so as to reduce the temperature of the biodiesel product from approximately 290° F. (143° C.) down to approximately 200-220° F. (93-105° C.), with about 210° F. (99° C.) being preferred, by transferring heat into a stripper feed stream. In a second cooling stage, a cooling water heat exchanger is used to further reduce the temperature of the biodiesel product 20 from approximately 210° F. (99° C.) down to approximately 80-90° F. (26-33° C.), with about 85° F. (30° C.) being preferred, by transferring heat into a cooling water recirculation loop. In a third cooling stage, a chilled fluid exchanger is used to further reduce the temperature of the biodiesel product 20 from approximately 85° F. (30° C.) down to approximately 65-75° F. (about 18-24° C.), with about 70° F. (22° C.) being preferred, by transferring heat into a chilled fluid recirculation loop, such as a solution of glycol and water. The minimum final cooled temperature should be no less than 40° F. (4° C.), such that the natural saturated fats of the oil do not crystallize.

At the conclusion of the cooling stage(s) 22, cooled biodiesel product is sent to a filter feed surge tank 26, as indicated by arrow B, for a sufficient time to allow the impurities and contaminants to solidify and precipitate in the form of particulates. Typically, the residence time in tank 26 is approximately 1-1½ hours. However, persons skilled in the art would readily appreciate that the biodiesel product may remain in the tank for shorter or longer periods of time depending upon a number of factors, including degree of impurities in the product, amount of product, degree of purity desired, convenience factors, etc. Depending upon the volume of the tank 26, the tank may be insulated or refrigerated to maintain the temperature of the biodiesel product.

After the sediments have formed in the biodiesel, the biodiesel product is transferred to a body feed tank 28, as represented by arrow C, wherein a filter aid from a feeder 30 is added to the biodiesel (arrow D), with about 0.1-0.25% by weight filter aid being preferred. Persons skilled in the art would readily understand that more or less filter aid may be added based on a number of factors, including source of feedstock, degree of filtration desired, convenience, cost, etc. One preferred filter aid is diatomaceous earth. Diatomaceous earth is characterized by high porosity, in that up to 85% of the volume of diatomaceous earth is made up of tiny inner connected pores and voids. Thus, diatomaceous earth has a high adsorption capacity, up to 100% of its weight in liquid, while still exhibiting properties of a dry powder. An agitator may be provided in the tank 28 to facilitate the mixing of the biodiesel, sediments, and diatomaceous earth into a slurry. Other conventional filtration materials may also be used instead of or in addition to the diatomaceous earth in this step, including sand, silica, or other finely graded materials. Such filtration materials are well known to persons skilled in the art, and include silica (of various grade sizes, and either inert or chemically activated), clay (such as acid-activated bleaching clay), cellulose, mined and milled volcanic deposits, minerals of all types (including perlite), and magnesium silicate (such a Magnesol sold by the Dallas Group).

Entrained biodiesel mist in the tank 28 may be removed by a demister 32 (arrow E) which in turn is connected to an external vent 34 (arrow F). Such mist droplets may be present in the air vapor exhaust which is vented during the filter blow-down and cake drying steps (described below), and preferably is removed via the demister 32 or other conventional means.

The biodiesel slurry is then piped to the filter 36 (arrows G and H) for removal of the particulates. Preferably, the filter 36 is a pressure leaf filter whose mesh screens have preferably been precoated with a similar media as that used in the filtration step. Other types of suitable filters for this step include, but are not limited to, pressure filters such as tube or candle filters, horizontal pressure filters, or filter presses. The diatomaceous earth or other filtration material previously added to the bulk biodiesel acts as a body feed that allows for the buildup of a filter cake on the leaves of the filter 36, thereby effectively removing the sediment in the biodiesel at the sub-micron level, while allowing the liquid biodiesel to pass through the cake with a minimal pressure drop. With a body feed addition of 0.1-0.25% diatomaceous earth by weight of biodiesel feed, for example, the filter 36 should be expected to run from 4 to 12 hours before cleaning is required. Cleaning of the filter 36 is accomplished using any convenient method known in the industry. Other filtration equipment using different types of media may also be utilized, such as carbon, activated charcoal, cloth or fabric (made of natural or synthetic materials), and ion exchange resin beads.

After the biodiesel product passes through the filter 36, quality may be tested. If the quality is insufficient, the product can be redirected to the tank 28, as indicated by arrow I, with further mixing with filtration material from the feeder 30 and further filtering through the filter 36.

In one series of preliminary tests utilizing 0.2% or less, by weight, of diatomaceous earth with biodiesel at a temperature cooled to at least 100° F. (38° C.), the pressure leaf filter 36 reduced water and sediment from the biodiesel product to less than 0.01% by weight. The tests imply, and conservatively support utilization of diatomaceous earth feed rate of about 186.6 grams/minute, with a biodiesel feed rate of approximately 554 pounds/minute to the filter 36 (i.e., about 0.019% diatomaceous earth body feed).

An initial filtration run was conducted for about 6 hours at the rate of 540 pounds/minute so as to result in approximately 197,000 pounds of biodiesel product being fed to the filtration assembly 36. Sediment and/or floaters for this period were noted as being absent altogether. Pressure loss across the filtration assembly 36 was noted at about 0.8 psi. After shutdown of the vertical leaf filter 36, draining, and 3-minute blow down, samples were obtained, with outstanding tests for the residual biodiesel oil, however, the "cake" was characterized as "dry".

Clean biodiesel product exiting the filter 36, and which does not need to be refiltered via line I, is then directed to a filtrate receiver surge tank 38, as indicated by arrow J. Tank 38 is optional, and provides for production control. The clean biodiesel is then directed to a final product filter 40, as indicated by arrow K. In one embodiment, the filter 40 may be sock filters, which remove any final particulates, including diatomaceous earth, in the biodiesel product. This final step polishes the biodiesel to final clarity and removes any residual diatomaceous earth or filter cake that may have passed through the mesh screens of the leaf filter 36. The polished biodiesel is sent to the appropriate storage tank 42 (arrow L) for certification and shipping.

Periodically, the leaf filter 36 must be cleaned. Cleaning or changing the pressure leaf filter 36 consists of taking the filter off-line, removing the liquid from the vessel, blowing the filter cake dry with air or nitrogen from a source 37 to minimize the loss of biodiesel product in the spent filter cake, and then discharging the dry filter cake from the screens. The filter 36 should be cleaned after a pre-set period of time, and when excessive pressure drop across the filter is noted during the operation. After cleaning, the filter 36 must be recharged with filtration material on the mesh leaves. Such recharging can be accomplished by circulating the biodiesel/filtration material slurry from a precoat feeder 44 which supplies filtration material to a biodiesel precoat tank 46, as indicated by arrow M. The slurry in the precoat tank 46 is then circulated through the leaf filter 36, as indicated by arrows P, H, and O until the filter leaves are sufficiently coated. Then, the normal filtration of biodiesel from the body feed tank 28 may continue. The slurry in the precoat tank 46 may also be vented through the demister 32, (discussed above) as indicated by arrow N.

The leaf filter pressure depends on numerous factors, such as equipment size, piping and flow parameters, and should be set according to their manufacturer's design specification. A pressure relief line (arrow Q) is provided to divert biodiesel from the leaf filter 36 back to the body feed tank 28 in the event of over pressure.

Periodically, the heat exchangers 24 need cleaning. In other industrial applications of heat exchangers, multiple heat exchangers have been used so that the cooling process may continue during the cleaning operation by shutting down the one heat exchanger while using the other heat exchanger. In the present invention, cleaning of the heat exchangers 24 does not require a shut down of one exchanger for cleaning while the other heat exchangers operate. Rather, cleaning is quickly and easily accomplished using a clean-in-place procedure by shutting off the flow of cooling fluid for a short period of time to the heat exchangers, while continuing to run the hot biodiesel product 20 through the heat exchangers, and then recycling the hot biodiesel through a recycle line 48, as indicated by arrows R and S. By running the hot biodiesel through the heat exchangers without cooling, any sediment buildup in the exchangers is dissolved in approximately one minute, or less, and thereby returns to suspension in the biodiesel product. After the exchangers 24 are cleaned, the coolant flow is restored to the exchangers 24 for the continued cooling of the biodiesel product 20, as described above.

It is understood that the various lines shown in FIG. 2 include valves and gauges for controlling and monitoring the flow of biodiesel during the cold filtration step 14.

The filtered and cleaned biodiesel may be tested to determine its quality, though such testing is not a required step in the cold filtration process.

One test method used to qualitatively determine filtration effectiveness and remaining sediment level in the finished product is to replicate the problematic storage and transportation conditions. This is achieved in the lab by cooling a 100 mL sample to 40° F. (4° C.) for 16 hours, then centrifuging the sample (per ASTM D-2709 test method) while still cold and visually inspecting the presence of sediment. The target product quality will have no visible sediment resulting from this test method. Alternatively, a sample can be allowed to freeze completely by subjecting it to 30° F. (−1° C.) or colder for 48 hours or more, then allowed to return to room temperature (approx. 75° F. or 24° C.). The sample is centrifuged as before and visually inspected for sediment. In all cases, the final product should be bright and clear with no visible sediment.

A more formalized test method was implemented in the State of Minnesota to "determine the mass of particulate contamination in a biodiesel fuel by filtration". This test method is a modified version of ASTM D-6217 and involves a cold soak of a 300 milliliter sample to 40° F. for 16 hours, followed by a natural warming to ambient temperature (70° F. or 21° C.), prior to filtering through a special lab apparatus. Technical staff on the National Biodiesel Board facilitated the modifications of this test method. All biodiesel fuel sold in Minnesota must pass this test with a filtration time of less than 360 seconds per the requirements of specific customers. Experience with this test has shown that the specification limits may not be adequate in identifying or preventing potential field problems, as either filtered or unfiltered fuels have easily passed this test.

Experience suggests the type and quality of the feedstock oil that is used to produce the biodiesel has an impact on the quantity and nature of sediment formed. Biodiesel made from refined and bleached soybean oil tends to form sediment more readily when exposed to instantaneous cooling. Biodiesel made from less processed soybean oil (such as degummed or deodorized) tends to require prolonged exposure to cooling temperatures before sediment will form. This time and temperature dependency on sediment formation could result in different field experiences with unfiltered fuel. However, it is noted that regardless of the feedstock oil used, the cold filtration process described above is successful at removing sediment-forming materials.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is as follows:

1. A method for removing impurities from biodiesel, comprising: producing biodiesel from a feedstock using a process with temperatures exceeding 380° C.; cooling the biodiesel to a temperature of between about 4-24° C. using at least one heat exchanger; directing the cooled biodiesel to a tank to allow impurities to precipitate as particulates in the biodiesel; and removing the precipitated particulates from the cooled biodiesel by passing the cooled biodiesel through a first filtering stage having a first filter and a second filtering stage having a second filter; wherein the first filter and the second filter are selected from a pressure filter and a sock filter.

2. The method of claim 1 whereby the biodiesel is cooled to a temperature of between about 4-22° C.

3. A method for removing impurities from biodiesel, comprising:
producing biodiesel from a feedstock using a process with temperatures exceeding 38° C.;
cooling the biodiesel in multiple stages using a series of heat exchangers to form particulates of impurities; and
filtering the cooled biodiesel to remove the particulates.

4. The method of claim 3 further comprising periodically cleaning the heat exchangers by running un-cooled biodiesel through the heat exchangers without supplying cooling fluid to the exchangers.

5. The method of claim 3 wherein a first cooling stage reduces the biodiesel temperature to approximately between 93-105° C., a second cooling stage further reduces the biodiesel temperature to approximately between 26-33° C., and a third cooling stage further reduces the biodiesel temperature to at least between 18-24° C.

6. The method of claim 1 wherein a first filtering stage includes the addition of a filter aid to the biodiesel.

7. The method of claim 6 whereby the filter aid is selected from the group consisting of diatomaceous earth, silica, sand, clay, cellulose, minerals, and mixtures thereof.

8. The method of claim 7 wherein the filter aid is diatomaceous earth.

9. The method of claim 8 wherein the diatomaceous earth is between 0.1% to 0.25% by weight of the biodiesel.

10. The method of claim 6 wherein the first filter is a leaf filter.

11. The method of claim 6 wherein a second filter is a sock filter.

12. A method for improving the quality of biodiesel fuel, comprising: producing biodiesel which conforms to the requirements of ASTM D6751-06 using a biodiesel manufacturing process; cooling the biodiesel to a temperature of less than 380° C. using at least one heat exchanger so as to precipitate out particles containing components other than methyl esters; and passing the biodiesel through at least a first filtering stage having a first physical filter and a second filter stage having a second physical filter to remove the particles containing components other than methyl esters and thereby produce improved biodiesel fuel; wherein the first physical filter and the second physical filter are selected from a pressure filter and a sock filter.

13. The method of claim 12 whereby the biodiesel is cooled to a temperature of between about 4-38° C.

14. The method of claim 12 wherein a first filtering stage includes the addition of a filter aid to the biodiesel.

15. The method of claim 14 whereby the filter aid is selected from the group consisting of diatomaceous earth, silica, sand, clay, cellulose, minerals, and mixtures thereof.

16. The method of claim 15 wherein the filter aid is diatomaceous earth.

17. The method of claim 16 wherein the diatomaceous earth is between 0.1% to 0.25% by weight of the biodiesel.

18. The method of claim 12 wherein the first physical filter is a leaf filter.

19. The method of claim 12 wherein the second physical filter is a sock filter.

20. The method of claim 12 whereby the biodiesel is cooled to a temperature of between about 4-22° C.

21. The method of claim 1 wherein the pressure filter is one of a leaf filter, a tube filter, a candle filter, a horizontal pressure filter, and a filter press.

22. The method of claim 12 wherein the pressure filter is one of a leaf filter, a tube filter, a candle filter, a horizontal pressure filter, and a filter press.

\* \* \* \* \*

UNITED STATES PATENT AND TRADEMARK OFFICE
CERTIFICATE OF CORRECTION

PATENT NO. : 11,326,115 B2
APPLICATION NO. : 14/809472
DATED : May 10, 2022
INVENTOR(S) : Myron Francis Danzer et al.

It is certified that error appears in the above-identified patent and that said Letters Patent is hereby corrected as shown below:

In the Claims

Column 6, Line 62, In Claim 1, "380°" should be --38°--.

Column 8, Line 5, In Claim 12, "380°" should be --38°--.

Signed and Sealed this
Twelfth Day of September, 2023

Katherine Kelly Vidal
*Director of the United States Patent and Trademark Office*